United States Patent [19]

Marshall

[11] Patent Number: 5,435,322
[45] Date of Patent: Jul. 25, 1995

[54] OPERATING ROOM RING STAND BASIN LINER/DRAPE

[75] Inventor: Lyman R. Marshall, Asheville, N.C.

[73] Assignee: Scherer Healthcare Ltd., Asheville, N.C.

[21] Appl. No.: 121,030

[22] Filed: Sep. 13, 1993

Related U.S. Application Data

[63] Continuation of Ser. No. 911,410, Jul. 10, 1992, abandoned.

[51] Int. Cl.⁶ .................... A61B 19/00; A47K 1/06
[52] U.S. Cl. ............................. 128/849; 4/655; 4/DIG. 18
[58] Field of Search ................... 128/849–856; 220/23.83; 4/550, 655, DIG. 18; 493/916; 224/4; 338/118

[56] References Cited

U.S. PATENT DOCUMENTS

| | | | |
|---|---|---|---|
| 430,195 | 6/1890 | Reimers | 4/655 |
| 758,770 | 5/1904 | McCann | 4/655 |
| 2,147,805 | 2/1939 | Windsor | 4/655 |
| 3,133,292 | 5/1964 | Spier | 4/580 |
| 3,650,267 | 3/1972 | Anderson | 128/853 |
| 3,668,050 | 6/1972 | Donnelly | 128/849 |
| 3,677,266 | 7/1972 | Green | 128/849 |
| 4,041,942 | 8/1977 | Dougan | 128/853 |
| 4,192,312 | 3/1980 | Wilson | 128/853 |
| 4,351,073 | 9/1982 | Elsas | 4/655 |
| 4,570,628 | 2/1986 | Neal | 128/853 |
| 4,903,710 | 2/1990 | Jessamine | 128/849 |
| 4,925,047 | 5/1990 | Valentine | 220/23.83 |
| 4,934,152 | 6/1990 | Templeton | 128/846 |
| 5,027,832 | 7/1991 | Williams | 128/849 |
| 5,109,873 | 5/1992 | Marshall | 128/849 |
| 5,140,996 | 8/1992 | Sommers | 128/849 |
| 5,163,299 | 11/1992 | Faries | 128/846 |
| 5,170,804 | 12/1992 | Glassman | 128/849 |

Primary Examiner—Michael A. Brown
Attorney, Agent, or Firm—Carter & Schnedler

[57] ABSTRACT

There is provided an operating room ring stand basin liner/drape which includes a plastic sheet having a tough middle portion formed in the shape of a ring stand basin for lining the inside of the basin and a drape portion attached to the formed portion so that the drape portion covers the legs of the ring stand. The sheet maintains a sterile field around the ring stand and basin and is disposed of after use so that there is no need to sterilize the basin after each use.

15 Claims, 3 Drawing Sheets

OPERATING ROOM RING STAND BASIN LINER/DRAPE

This is a Continuation of application Ser. No. 07/911,410 filed Jul. 10, 1992, now abandoned.

BACKGROUND OF THE INVENTION

This invention relates to apparatus which is used in an operating room. More particularly it relates to ring stands and ring stand basins.

Ring stand basins, which are normally made of stainless steel, are used by surgeons and other operating room personnel to remove blood and other bodily fluids from instruments during a surgical procedure. During use the basin is partially filled with a sterile saline solution. The stainless steel basin is received in a ring stand. The ring stand is also normally made of stainless steel and includes a ring through which the basin is received and four legs which are attached to the ring. The legs elevate the ring, and thus the basin, to a level where it may be used by the surgical personnel.

The basin must be sterilized after each use, however the ring stand is not normally sterilized after each use. Therefore a drape which is referred to as CSR wrap is placed between the bottom of the basin and the ring stand. The CSR wrap is of sufficient size so as to cover the legs of the ring stand thereby maintaining a sterile field around the ring stand. One example of such a ring stand basin/CSR wrap setup is shown in U.S. Pat. No. 4,925,047 issued to Valentine.

A surgical basin is normally 13" in diameter and 4" deep and thus is a substantially large item to be sterilized. Normally sterilization costs are measured by the volume of the apparatus which is sterilized. Thus it is expensive to sterilize bulky items such as basins after each usage. In addition, CSR wrap is not an inexpensive item often costing 50¢ per sheet.

In order to alleviate the need to sterilize the stainless steel ring basin, disposable plastic basins have been substituted for the stainless steel ring basin. While the cost of sterilizing the stainless steel basin is saved, the plastic basins are expensive, normally costing approximately $2.00 to $2.50 each in a sterile pack, which includes CSR wrap. The plastic basin must be a rather sturdy and substantial device to hold the saline and thick enough to inhibit sharp instruments from puncturing the plastic. If the plastic basin is punctured, liquids from the basin would spill to the operating room floor creating a hazard during the surgical procedure. In addition, because of the size of the plastic basin/CSR pack, sterilization, shipping, storage and disposal costs are high. Thus it is desirable to have a ring stand basin setup which overcomes the problems set forth above.

OBJECTS OF THE INVENTION

It is therefore one object of this invention to provide a ring stand basin apparatus which avoids the need for sterilization of the basin yet is inexpensive to produce and easy to use.

It is another object to reduce the cost and the disposal problems associated with plastic basins and CSR wraps.

SUMMARY OF THE INVENTION

In accordance with one form of this invention there is provided an operating room basin liner/drape including a sheet having a formed portion and a drape portion. Preferably the formed portion is made of thicker material than the drape portion. The formed portion is in the shape of a basin for lining the inside of a basin. The drape portion is attached to the formed portion. The drape portion surrounds the ring stand on all sides and covers the legs of the ring stand. Thus a sterile field is maintained about the entire ring stand and basin. After the surgical procedure the entire sheet may be disposed of and there is no need to sterilize the basin. The basin liner/drape avoids the costs associated with sterilization of the basin and further avoids the need for a separate CSR wrap for maintaining a sterile field about the remainder of the ring stand. In addition, while the formed portion is thick, it may be folded along with the drape portion for shipping and storage. The basin liner/drape is much smaller and lighter than a package comprising a rigid plastic basin and CSR wrap. Also, the overall size, and thus the cost, of the drape portion as compared to the CSR wrap is substantially reduced.

BRIEF DESCRIPTION OF THE DRAWINGS

The subject matter which is regarded as the invention is set forth in the appended claims. The invention itself, however, together with further objects and advantages thereof, may be better understood by reference to the following description taken in conjunction with the accompanying drawings in which:

DESCRIPTION OF THE PREFERRED EMBODIMENT

Figure 1:
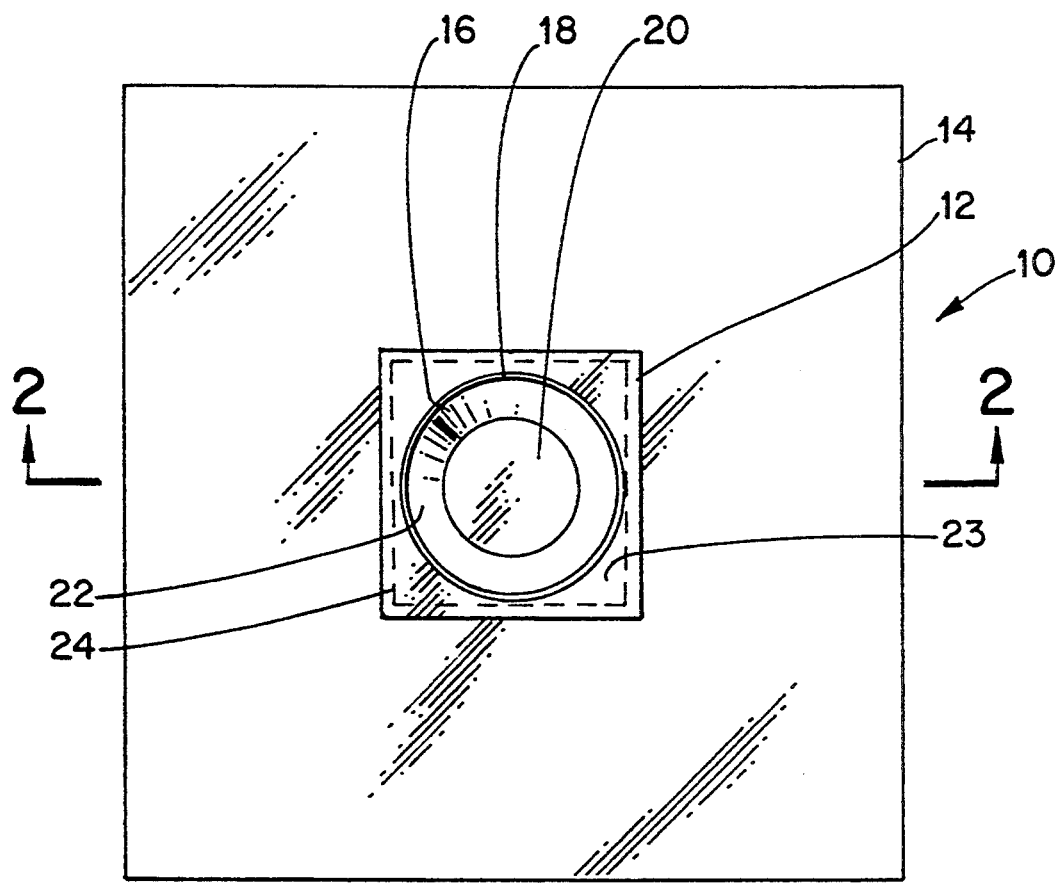
FIG. 1 is a plan view of the operating room basin liner/drape of the subject invention.
Figure 2:
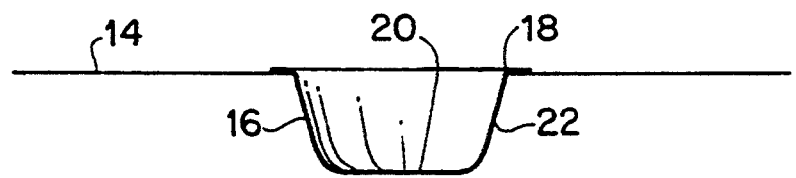
FIG. 2 is a sectional view of FIG. 1 taken through Section lines 2—2.
Figure 3:
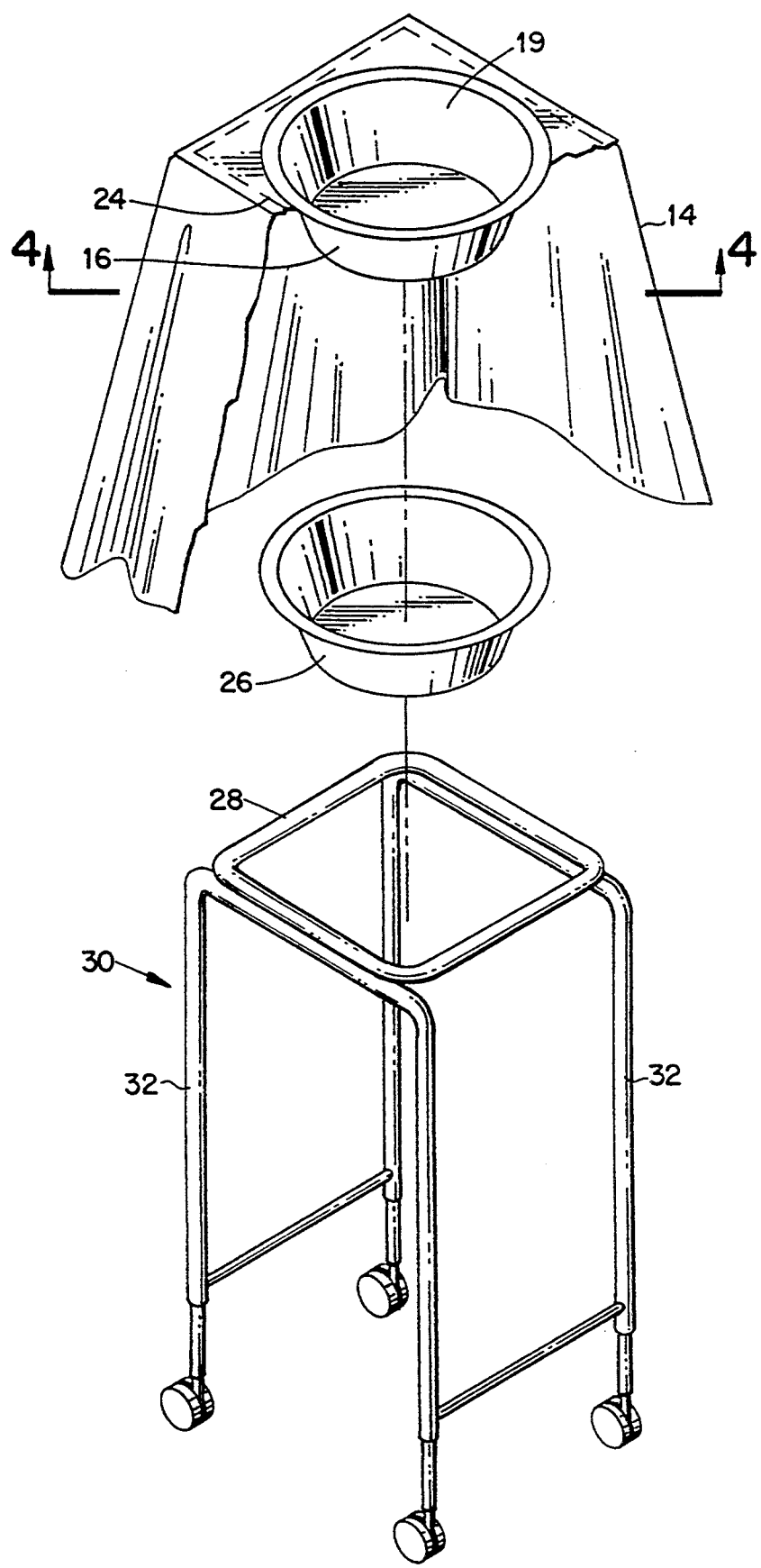
FIG. 3 is an exploded view showing the apparatus of FIG. 1 with portions removed for clarity together with a typical basin and ring stand.
Figure 4:
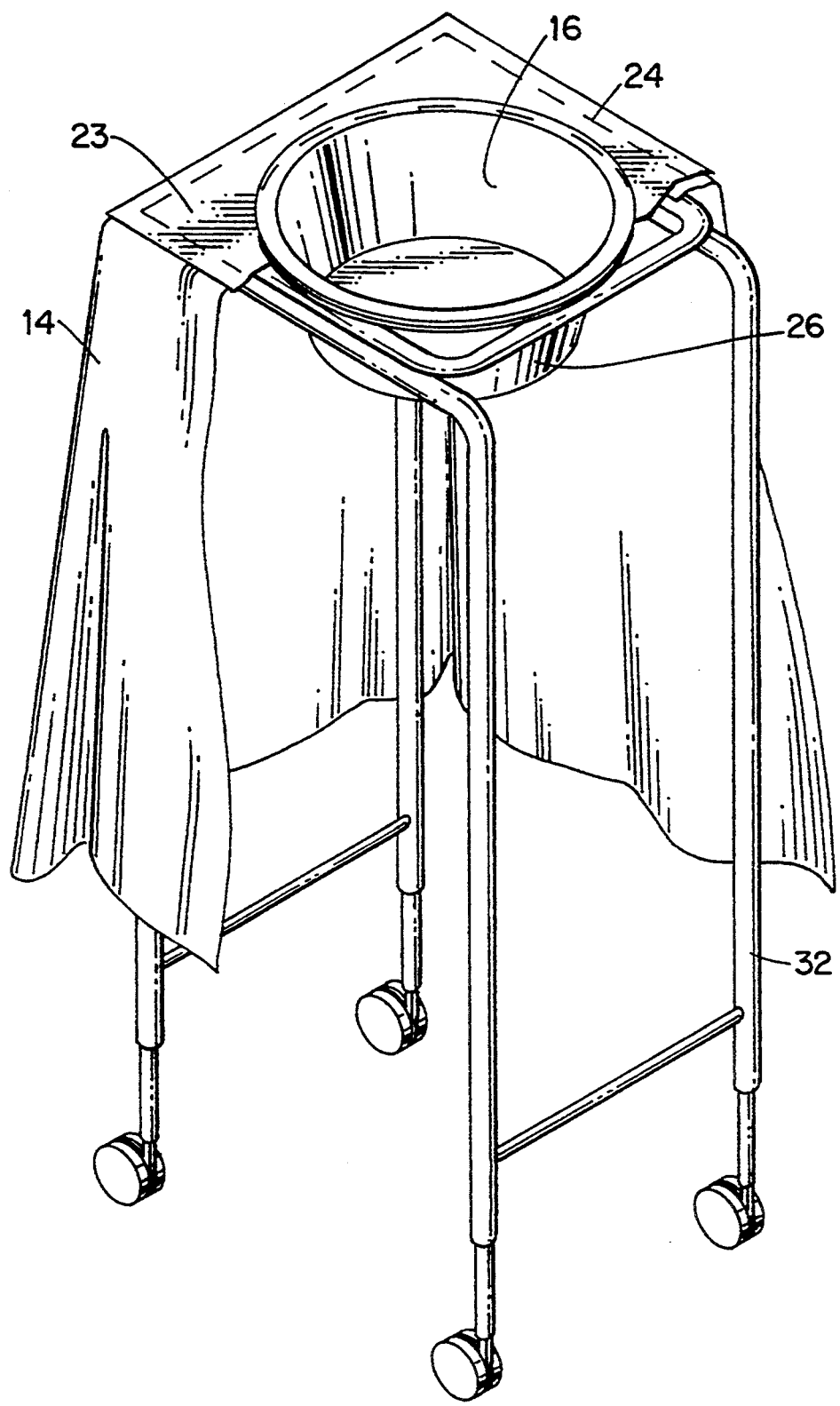
FIG. 4 is a sectional view of FIG. 3 taken through Section lines 4—4, however with the basin received in the ring stand and the basin liner received in the basin.

Referring now more particularly to FIGS. 1 through 4, there is provided a basin liner/drape in the form of sheet 10 which includes formed portion 12 and drape portion 14. Formed portion 12 is preferably made of a heavy gauge polyethylene/ionomer resin blend which should be between 10 and 16 mils. in thickness but preferably is 13 mils. The preferred ionomer resin is Surlyn which is commercially available from DuPont. The percentage of the ionomer resin in the blend should be between 40% and 70%. The ionomer resin adds substantial toughness to the polyethylene. Formed portion includes basin liner 16 which is frustroconical in shape, but hollow, having lip 18 about opening 19, bottom 20, and sloping side 22. The basin liner portion 16 is formed in a standard vacuum forming apparatus.

The drape portion 14 is preferably made of a light gauge polyethylene which should be between 1.5 and 2.5 mils. in thickness, but preferably is 2 mils. thick. The drape portion 14 is bonded to the formed portion 12 at the junction indicated by liner 24 by thermal bonding or other known techniques. In the preferred embodiment the formed portion 12 extends beyond lip 18 resulting in a planar region made of the thicker polyethylene/ionomer resin blend so that instruments may be laid thereon. This thick tough planar region also prevents penetration of the sterile field.

Basin liner portion 16 is adapted to be received inside of stainless steel basin 26. Stainless steel basin 26 in turn is received inside of ring 28 of ring stand 30. Ring stand 30 includes legs 32 to elevate the ring 28 and thus basin 26 to the appropriate level for use in the operating room. The drape portion 14 covers the legs 32 of the ring stand, thereby providing a sterile field around the ring stand.

Once the basin liner 16 is placed inside of basin 26, sterile saline solution is added to the basin liner and surgical instruments may be rinsed within the basin liner during the surgical procedure. Once the procedure has been completed, the entire sheet 10 may be disposed of. Since a sterile field was maintained about the basin 26, there is no need to sterilize the basin after each procedure.

Thus by utilizing the above-described operating room basin liner/drape, the expense of sterilizing the basin is obviated and ring stand. In addition there is no need for a bulky and heavy disposable plastic basin/CSR wrap pack thereby reducing shipping, storage, disposal and sterilization costs. The above-described operating room basin liner/drape is ⅓ of the weight and costs five times less to sterilize than the prior art basin/CSR wrap.

From the foregoing description of the preferred embodiment of the invention, it will be apparent that many modifications may be made therein without departing from the true spirit and scope of the invention. It is intended in the appended claims to cover all such modifications which fall within the true spirit and scope of the invention.

I claim:

1. An operating room basin liner/drape comprising:
   a sheet; said sheet having a formed portion; said formed portion being in the shape of a basin for lining the inside of a circular shaped basin;
   said sheet including a drape portion attached to said formed portion; said formed portion not having any holes therein, thereby forming a seal; the material in the formed portion is substantially thicker than the material in the drape portion.

2. A basin liner as set forth in claim 1 wherein said formed portion is stiff and said drape portion is loose.

3. A basin liner as set forth in claim 2 wherein said sheet is made of plastic material; said plastic in said formed portion being thicker than the plastic in said drape portion.

4. A basin liner as set forth in claim 3 wherein said formed portion is made of a blend of polyethylene and ionomer resin.

5. A basin liner as set forth in claim 4 wherein thickness of said formed portion is between 10 and 16 mil. and the thickness of said drape portion is between 1.5 and 2.5 mils.

6. A basin liner as set forth in claim 1 wherein said formed portion includes a circular lip and a round planar bottom; a sloping sidewall connecting said lip to said bottom; said drape portion extending from said lip.

7. A basin liner as set forth in claim 6 wherein said formed portion extends beyond said lip forming a planar region.

8. A basin liner as set forth in claim 1 wherein a basin is adapted to be received in a ring stand having legs; said drape portion substantially covering the legs of the ring stand thereby maintaining a sterile field about said ring stand.

9. An operating room ring stand apparatus comprising:
   a ring stand having a ring and a plurality of legs extending therefrom;
   a circular shaped basin adapted to be received in said ring;
   a sheet; said sheet having a formed portion; said formed portion being in the shape of a basin for lining the inside of said basin; said sheet including a drape portion attached to said formed portion; said formed portion not having any holes therein, thereby forming a seal; the material in the formed portion is substantially thicker than the material in the drape portion.

10. An apparatus as set forth in claim 9 wherein said formed portion is stiff and said drape portion is loose.

11. An apparatus as set forth in claim 10 wherein said sheet is made of a plastic material; said formed portion being of a heavier gauge than said drape portion.

12. An apparatus as set forth in claim 11 wherein said formed portion is made of a blend of polyethylene and ionomer resin.

13. An apparatus as set forth in claim 12 wherein the thickness of the formed portion is between 10 and 16 mils. and the thickness of the drape portion is between 1.5 and 2.5 mils.

14. An apparatus as set forth in claim 9 wherein said formed portion includes a circular lip and a round planar bottom; a sloping sidewall connecting said lip to said bottom; said drape portion extending from said lip.

15. An apparatus as set forth in claim 14 wherein said formed portion extends beyond said lip.

* * * * *